US009693978B2

(12) United States Patent
Chidambaram et al.

(10) Patent No.: US 9,693,978 B2
(45) Date of Patent: *Jul. 4, 2017

(54) SOLVENT SYSTEM FOR ENHANCING THE SOLUBILITY OF PHARMACEUTICAL AGENTS

(71) Applicant: Banner Life Sciences LLC, High Point, NC (US)

(72) Inventors: Nachiappan Chidambaram, Salt Lake City, UT (US); Aqeel Fatmi, Greensboro, NC (US)

(73) Assignee: Banner Life Sciences LLC, High Point, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/977,808

(22) Filed: Dec. 22, 2015

(65) Prior Publication Data

US 2016/0106841 A1 Apr. 21, 2016

Related U.S. Application Data

(63) Continuation of application No. 11/367,238, filed on Mar. 3, 2006, now abandoned.

(60) Provisional application No. 60/659,679, filed on Mar. 3, 2005.

(51) Int. Cl.
| *A61K 31/192* | (2006.01) |
| *A61K 9/48* | (2006.01) |
| *A61K 31/765* | (2006.01) |
| *A61K 47/12* | (2006.01) |
| *A61K 9/50* | (2006.01) |
| *A61K 9/00* | (2006.01) |

(52) U.S. Cl.
CPC .......... *A61K 31/192* (2013.01); *A61K 9/0053* (2013.01); *A61K 9/4825* (2013.01); *A61K 9/4833* (2013.01); *A61K 9/4858* (2013.01); *A61K 9/4866* (2013.01); *A61K 9/50* (2013.01); *A61K 9/5089* (2013.01); *A61K 31/765* (2013.01); *A61K 47/12* (2013.01)

(58) Field of Classification Search
None
See application file for complete search history.

(56) References Cited

U.S. PATENT DOCUMENTS

| 5,071,643 A | 12/1991 | Patel | |
| 5,360,615 A * | 11/1994 | Yu ........................ | A61K 9/2009 424/455 |
| 5,484,606 A | 1/1996 | Dhabar | |
| 5,505,961 A | 4/1996 | Shelly | |
| 5,541,210 A | 7/1996 | Cupps | |
| 5,648,358 A | 7/1997 | Mitra | |
| 5,885,608 A | 3/1999 | McEntee | |
| 5,912,011 A | 6/1999 | Makin | |
| 6,287,594 B1 | 9/2001 | Meyer | |
| 6,365,180 B1 | 4/2002 | Wilson | |
| 6,383,515 B2 | 5/2002 | Sawyer | |
| 6,387,400 B1 | 5/2002 | Webster | |
| 6,689,382 B2 | 2/2004 | Berthel | |
| 7,101,572 B2 | 9/2006 | Santos | |
| 2001/0007668 A1 | 7/2001 | Sawyer | |
| 2002/0187195 A1 | 12/2002 | Sawyer | |
| 2004/0157928 A1 | 8/2004 | Kim | |
| 2005/0158377 A1 * | 7/2005 | Popp ..................... | A61K 9/4866 424/451 |
| 2006/0099246 A1 * | 5/2006 | Tanner ................. | A61K 9/4816 424/451 |

FOREIGN PATENT DOCUMENTS

WO 9531979 11/1995

OTHER PUBLICATIONS

Wikipedia (https://en.wikipedia.org/wiki/Conjugate_acid (downloaded on Jul. 8, 2016).*
Wikipedia "Self-ionization of water", http://en.wikipedia.org/wiki/Self-ionization_of_water, Accessed Mar. 2010.

* cited by examiner

*Primary Examiner* — Jake Vu
(74) *Attorney, Agent, or Firm* — Brinks Gilson & Lione

(57) ABSTRACT

Liquid and semi-solid pharmaceutical compositions, which can be administered in liquid form or can be used for preparing capsules, are described herein. The composition comprises the salt of one ore more active agents, polyethylene glycol, 0.2-1.0 mole equivalents of a de-ionizing agent per mole of active agent, and water. The pH of the composition is adjusted within the range of 2.5-7.5. The de-ionizing agent causes partial de-ionization (neutralization) of the salt of the active agent resulting in enhanced bioavailability of salts of weakly acidic, basic or amphoteric active agents as well as lesser amounts of polyethylene glycol (PEG) esters.

38 Claims, No Drawings

SOLVENT SYSTEM FOR ENHANCING THE SOLUBILITY OF PHARMACEUTICAL AGENTS

CROSS REFERENCE TO RELATED APPLICATIONS

The present application is a continuation of U.S. application Ser. No. 11/367,238, filed Mar. 3, 2006, which is related to and claims priority under 35 U.S.C. §119(e) to U.S. provisional patent application U.S. Ser. No. 60/659,679 entitled "Solvent System for Enhancing the Solubility of Pharmaceutical Agents", filed Mar. 8, 2005. The entire contents of these applications are incorporated herein by reference.

FIELD OF THE INVENTION

This invention is in the field of fill materials encapsulated in soft gelatin capsules.

BACKGROUND OF THE INVENTION

Filled one-piece soft gelatin capsules ("softgels") have been widely used for years to encapsulate consumable materials such as vitamins and pharmaceuticals in a liquid vehicle or carrier. Because softgels have properties which are quite different from two-piece hardshell capsules, softgels are more capable of retaining a liquid fill material.

Not all liquids may be enclosed in a softgel capsule. Liquids containing more than about 20% water by weight are generally not enclosed in softgels, because the water tends to dissolve the gelatin shell. Other solvents such as propylene glycol, glycerin, low molecular weight alcohols, ketones, acids, amines, and esters all tend to degrade or dissolve the gelatin shell to some extent.

Softgels are also somewhat sensitive to pH, and generally require a pH in the encapsulated liquid from about 2.5 to about 7.5. Highly acidic liquids may hydrolyze the gelatin, resulting in leaks, while basic liquids may tan the gelatin, resulting in decreased solubility of the gelatin shell.

Pharmaceutical liquids are usually enclosed in softgels as either viscous solutions or suspensions. Suspensions are pharmaceutically less desirable because they can settle during manufacture, which leads to a less uniform product. In contrast, solutions provide the best liquid form for obtaining optimal "content uniformity" in a batch. Further, solutions typically provide a faster and more uniform absorption of an active agent than do suspensions.

Suitable softgel solutions, however, can be difficult to achieve. One constraint is size. Many pharmaceutical agents require volumes of solvent too large to produce a softgel capsule small enough to be taken by patients. The solvent must also have sufficient solvating power to dissolve a large amount of the pharmaceutical agent to produce a concentrated solution and yet not dissolve, hydrolyze or tan the gelatin shell.

Concentrated solutions of pharmaceutical agents for use in softgel capsules have been described. Most of these systems involve ionizing the free pharmaceutical agent in situ to the corresponding salt. For example, U.S. Pat. No. 5,360,615 to Yu et al. discloses a solvent system for enhancing the solubility of acidic, basic, or amphoteric pharmaceutical agents. The solvent system comprises polyethylene glycol, an ionizing agent, and water. The ionizing agent functions by causing the partial ionization of the free pharmaceutical agent. U.S. Pat. No. 6,383,515, U.S. Patent Application Publication No. 2002/0187195, and U.S. Patent Application Publication No. 2001/0007668 to Sawyer et al. discloses pharmaceutically acceptable solutions containing a medicament suitable for filling softgel capsules comprising a polymer such as polyethylene glycol and an acid salt of a compound having three or more carbon atoms, such as sodium propionate. The salt helps to ionize the medicament without relying on the use of strong acids or bases. U.S. Pat. No. 6,689,382 to Berthel et al. describes a pharmaceutical formulation suitable for filling softgel capsules comprising (a) a therapeutically effective amount of a non-steroidal anti-inflammatory drug (NSAID); and (b) a solvent system comprising 40% to 60% by weight a polyoxyethylene ether, 15% to 35% by weight of glycerin and 15% to 35% by weight water. In cases where the NSAID has a carboxyl or an acidic functional group, the solvent system also includes hydroxide ions. U.S. Pat. No. 5,505,961 to Shelley et al. describes a method for increasing the solubility of acetaminophen alone or in combination with other pharmaceutically active agents to form a clear solution for encapsulation into a softgel capsule. The method comprises solubilizing acetaminophen in a mixture of propylene glycol, polyethylene glycol, water, polyvinylpyrrolidone and sodium or potassium acetate.

The previously described methods all involve the conversion of the free pharmaceutical agent to the corresponding salt. In cases where the free pharmaceutical agent is acidic, the resulting anion can react with the polyethylene glycol in the fill to produce polyethylene glycol esters, thus reducing the amount of available pharmaceutical agent.

There is a need for a solvent system containing a medicament, which can be encapsulated in a softgel capsule, wherein the formation of PEG esters is minimized.

Therefore it is an object of the invention to provide a stable solvent system for pharmaceutical agents, which is suitable for encapsulation in a softgel capsule, wherein the formation of PEG esters is minimized.

BRIEF SUMMARY OF THE INVENTION

Liquid and semi-solid pharmaceutical compositions, which can be administered in liquid form or can be used for preparing capsules, are described herein. The composition comprises the salt of one or more active agents, and 0.2-1.0 mole equivalents of a de-ionizing agent per mole of active agent. The pH of the composition is adjusted within the range of 2.5-7.5. The de-ionizing agent causes partial de-ionization (neutralization) of the salt of the active agent resulting in enhanced bioavailability of salts of weakly acidic, basic or amphoteric active agents as well as decreased amounts of polyethylene glycol (PEG) esters.

DETAILED DESCRIPTION OF THE INVENTION

I. Composition
  A. Fill Materials
  1. Drugs to be Formulated

The formulation can contain any therapeutic, diagnostic, prophylactic or nutraceutical agent. Exemplary agents include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; anti-inflammatory agents; antimigraine agents; antineoplastic agents; antiparkinson drugs; antipruritic agents; antipsychotic agents; antipyretic agents; antispasmodic agents; antitubercular agents; antiulcer agents; antiviral agents; anxiolytic agents; appetite suppressants (anorexic agents); attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; sialagogues, steroids; smoking cessation agents; sympathomimetics; tranquilizers; vasodilators; beta-agonist; and tocolytic agents.

A first class of drugs is selected based on inclusion in the molecule of a weakly acidic, basic or amphoteric group that can form a salt. Any drug that bears an acidic or a basic functional group, for example, an amine, imine, imidazoyl, guanidine, piperidinyl, pyridinyl, quaternary ammonium, or other basic group, or a carboxylic, phosphoric, phenolic, sulfuric, sulfonic or other acidic group, can react with the de-ionizing agent.

Some specific drugs that bear acidic or basic functional groups and thus may be converted to the corresponding salt for use in the described formulations include, but are not limited to, Acetaminophen, Acetylsalicylic acid, Alendronic acid, Alosetron, Amantadine, Amlopidine, Anagrelide, Argatroban, Atomoxetine, Atrovastatin, Azithromycin dehydrate, Balsalazide, Bromocriptan, Bupropion, Candesartan, Carboplatin, Ceftriaxone, Clavulonic acid, Clindamycin, Cimetadine, Dehydrocholic (acid), Dexmethylphenidate, Diclofenac, Dicyclomine, Diflunisal, Diltiazem, Donepezil, Doxorubicin, Doxepin, Epirubicin, Etodolic acid, Ethacrynic acid, Fenoprofen, Fluoxetine, Flurbiprofen, Furosemide, Gemfibrozil, Hydroxyzine, Ibuprofen, Imipramine, Indomethacin, Ketoprofen, Levothyroxine, Maprolitline, Meclizine, Methadone, Methylphenidate, Minocycline, Mitoxantone, Moxifloxacin, Mycophenolic acid, Naproxen, Niflumic acid, Ofloxacin, Ondansetron, Pantoprazole, Paroxetine, Pergolide, Pramipexole, Phenytoin, Pravastain, Probenecid, Rabeprazole, Risedronic acid, Retinoic acid, Ropinirole, Selegiline, Sulindac, Tamsulosin, Telmisertan, Terbinafine, Theophyline, Tiludronic Acid, Tinzaparin, Ticarcillin, Tometin, Valproic acid, Salicylic acid, Sevelamer, Ziprasidone, Zoledronic acid, Acetophenazine, Albuterol, Almotriptan, Amitriptyline, Amphetamine, Atracurium, Beclomethasone, Benztropine, Biperiden, Bosentan, Bromodiphenhydramine, Brompheniramine carbinoxamine, Caffeine, Capecitabine, Carbergoline, Cetirizine, Chlocylizine, Chlorpheniramine, Chlorphenoxamine, Chlorpromazine, Citalopram, Clavunate potassium, Ciprofloxacin, Clemastine, Clomiphene, Clonidine, Clopidogrel, Codeine, Cyclizine, Cyclobenzaprine, Cyproheptadine, Delavirdine, Diethylpropion, Divalproex, Desipramine, Dexmethylphenidate, Dexbrompheniramine, Dexchlopheniramine, Dexchlor, Dextroamphetamine, Dexedrine, Dextromethorphan, Fiflunisal, Diphemanil methylsulphate, Diphenhydramine, Dolasetron, Doxylamine, Enoxaparin, Ergotamine, Ertepenem, Eprosartan, Escitalopram, Esomeprazole, Fenoldopam, Fentanyl, Fexofenadine, Flufenamic acid, Fluvastatin, Fluphenazine, Fluticasone, Fosinopril, Frovatriptan, Gabapentin, Galatamine, Gatifloxacin, Gemcitabine, Haloperidol, Hyalurondate, Hydrocodone, Hydroxychloroquine, Hyoscyamine, Imatinib, Imipenem, Ipatropin, Lisinopril, Leuprolide, Levopropoxyphene, Losartan, Meclofenamic acid, Mefanamic acid, Mesalamine, Mepenzolate, Meperidine, Mephentermine, Mesalimine, Mesoridazine, Metaproteranol, Metformin, Methdialazine, Methscopolamine, Methysergide, Metoprolol, Metronidazole, Mibefradil, Montelukast, Morphine, Mometasone, Naratriptan, Nelfinavir, Nortriptylene, Noscapine, Nylindrin, Omeprazole, Orphenadrine, Oseltamivir, Oxybutynin, Papaverine, Pentazocine, Phendimetrazine, Phentermine, Pioglitazone, Pilocarpine, Prochloroperazine, Pyrilamine, Quetapine, Ranitidine, Rivastigmine, Rosiglitazone, Salmetrol, Sertaline, Sotalol, Sumatriptan, Tazobactam, Tacrolimus, Tamoxifen, Ticlopidine, Topiramate, Tolterodine, Triptorelin, Triplennamine, Triprolidine, Tramadol, Trovofloxacin, Ursodiol, Promazine, Propoxyphene, Propanolol, Pseudoephedrine, Pyrilamine, Quinidine, Oxybate sodium, Sermorelin, Tacrolimus, Tegaseroid, Teriparatide, Tolterodine, Triptorelin pamoate, Scopolamine, Venlafaxine, Zamivir, Aminocaproic acid, Aminosalicylic acid, Hydromorphone, Isosuprine, Levorphanol, Melhalan, Nalidixic acid, and Para-aminosalicylic acid.

2. Deionizing Agent

The deionizing agent functions by causing partial deionization (neutralization) of the salt of one or more pharmaceutically active agents. When the active agent is the salt of a weak acid and a strong base, the deionizing agent is preferably a hydrogen ion species. When the active agent is the salt of a weak base and a strong acid, the deionizing agent is preferably a hydroxide ion species. The deionizing agent is preferably present in an amount between 0.2 to 1.0 mole equivalents per mole of the pharmaceutically active agent.

Exemplary hydrogen ion species useful as de-ionizing agents described herein, include, but are not limited to, hydrochloric acid, hydrobromic acid, hydroiodic acid, sulfuric acid, fumaric acid, maleic acid, tartaric acid, methane-, ethane-, and benzene sulfonates, citric acid, malic acid, acetic acid, proprionic acid, pyruvic acid, butanoic acid, and lactic acid.

Exemplary hydroxide ion species useful as de-ionizing agents described herein, include, but are not limited to, metal hydroxides such as sodium hydroxide, potassium hydroxide, ammonium hydroxide, calcium hydroxide, aluminum hydroxide, and magnesium hydroxide.

Additional acid or base can be added to adjust the pH of the fill composition. In a preferred embodiment, the pH of the fill composition is from about 2.5 to about 7.5.

3. Excipients

Formulations may be prepared using a pharmaceutically acceptable carrier composed of materials that are considered safe and effective and may be administered to an individual without causing undesirable biological side effects or unwanted interactions. The carrier is all components present in the pharmaceutical formulation other than the active ingredient or ingredients. As generally used herein "carrier" includes, but is not limited to, plasticizers, crystallization inhibitors, wetting agents, bulk filling agents, solubilizers, bioavailability enhancers, solvents, pH-adjusting agents and combinations thereof.

In a preferred embodiment, a mixture of polyethylene glycol and water is used as a solvent for the salt of the active agent and the de-ionizing agent. Polyethylene glycol is present in an amount from about 10% to about 80% by weight. Water is present in an amount from about 1% to 18% by weight. The molecular weight of polyethylene glycol is between 300 and 1500. Other suitable solvents include surfactants and copolymers of polyethylene glycol. Optionally, glycerin, polyvinyl pyrrolidone (PVP) or propylene glycol (PPG) can be added to enhance the solubility of the drug agent.

B. Shell Composition

1. Gelatin

Gelatin is the product of the partial hydrolysis of collagen. Gelatin is classified as either Type A or Type B gelatin. Type A gelatin is derived from the acid hydrolysis of collagen while Type B gelatin is derived from alkaline hydrolysis of collagen. Traditionally, bovine bones and skins have been used as raw materials for manufacturing Type A and Type B gelatin while porcine skins have been used extensively for manufacturing Type A gelatin. In general acid-processed gelatins form stronger gels than lime-processed gelatins of the same average molecular weight.

2. Other Shell Additives

Other suitable shell additives include plasticizers, opacifiers, colorants, humectants, preservatives, flavorings, and buffering salts and acids.

Plasticizers are chemical agents added to gelatin to make the material softer and more flexible. Suitable plasticizers include glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

II. Method of Making

A. Fill Material

The fill material is prepared by mixing the agent (such as a salt of the drug), the deionizing agent, water, and polyethylene glycol at a temperature of 50° C. to 70° C. The resulting solution is encapsulated using the appropriate gel mass. The pharmaceutical agent is present in an amount from about 10% to about 50% by weight. The deionizing agent is present in an amount from about 0.2 to 1.0 mole per mole of the pharmaceutical agent. Water is present in an amount from about 1% to about 20% by weight and polyethylene glycol is present in amount from about 10% to about 80% by weight. Optionally, propylene glycol and/or polyvinyl pyrrolidone are present in an amount from about 1% to about 10%.

B. Gel Mass

The main ingredients of the softgel capsule shell are gelatin, plasticizer, and purified water. Typical gel formulations contain (w/w) 40-50% gelatin, 20-30% plasticizer, and 30-40% purified water. Most of the water is subsequently lost during capsule drying. The ingredients are combined to form a molten gelatin mass using either a cold melt or a hot melt process. The prepared gel masses are transferred to preheated, temperature-controlled, jacketed holding tanks where the gel mass is aged at 50-60° C. until used for encapsulation.

1. Cold Melt Process

The cold melt process involves mixing gelatin with plasticizer and chilled water and then transferring the mixture to a jacket-heated tank. Typically, gelatin is added to the plasticizer at ambient temperature (18-22° C.). The mixture is cooked (57-95° C.) under vacuum for 15-30 minutes to a homogeneous, deaerated gel mass. Additional shell additives can be added to the gel mass at any point during the gel manufacturing process or they may be incorporated into the finished gel mass using a high torque mixer.

2. Hot Melt Process

The hot melt process involves adding, under mild agitation, the gelatin to a preheated (60-80° C.) mixture of plasticizer and water and stirring the blend until complete melting is achieved. While the hot melt process is faster than the cold melt process, it is less accurately controlled and more susceptible to foaming and dusting.

C. Softgel Capsule

Softgel capsules are typically produced using a rotary die encapsulation process. The gel mass is fed either by gravity or through positive displacement pumping to two heated (48-65° C.) metering devices. The metering devices control the flow of gel into cooled (10-18° C.), rotating casting drums. Ribbons are formed as the cast gel masses set on contact with the surface of the drums.

The ribbons are fed through a series of guide rolls and between injection wedges and the capsule-forming dies. A food-grade lubricant oil is applied onto the ribbons to reduce their tackiness and facilitate their transfer. Suitable lubricants include mineral oil, medium chain triglycerides, and soybean oil. Fill formulations are fed into the encapsulation machine by gravity. In the preferred embodiment, the softgels contain printing on the surface, optionally identifying the encapsulated agent and/or dosage.

III. Method of Use

The softgels may be used to encapsulate a wide range of pharmaceutically active agents, nutritional agents and personal care products. Softgel capsules may be administered orally to a patient to deliver a pharmaceutically active agent.

EXAMPLES

In the following examples, the fill material can be prepared by mixing the salt of one or more pharmaceutically active agents, the deionizing agent, water and polyethylene glycol at a temperature of 50° C. to 70° C. The resulting solution can be encapsulated in a softgel capsule using the appropriate gel mass.

Example 1. Naproxen Sodium with Acetic Acid as the Deionizing Agent

Fill Material:

| Ingredients | % (by weight) |
| --- | --- |
| Naproxen Sodium | 25.50 |
| Acetic Acid | 3.00 |
| PVP | 1.85 |

-continued

| Ingredients | % (by weight) |
|---|---|
| PEG 400 | 62.30 |
| Water | 7.40 |

Example 2. Naproxen Sodium with Citric Acid as the Deionizing Agent

Fill Material:

| Ingredients | % (by weight) |
|---|---|
| Naproxen Sodium | 25.50 |
| Citric Acid | 4.75 |
| PVP | 1.85 |
| PEG 400 | 60.50 |
| Water | 7.40 |

Example 3. Naproxen Sodium with Hydrochloric Acid as the Deionizing Agent

Fill Material:

| Ingredients | % (by weight) |
|---|---|
| Naproxen Sodium | 25.50 |
| Hydrochloric Acid | 4.72 |
| PVP | 1.85 |
| PEG 400 | 63.52 |
| Water | 7.40 |

Example 4. Naproxen Sodium with Acetic Acid as the Deionizing Agent

Fill Material:

| Ingredients | % (by weight) |
|---|---|
| Naproxen Sodium | 25.50 |
| Acetic Acid | 3.00 |
| PVP | 1.85 |
| PEG 400 | 31.15 |
| Water | 7.40 |
| PEG 600 | 31.15 |

Example 5. Naproxen Sodium with Citric Acid as the Deionizing Agent

Fill Material:

| Ingredients | % (by weight) |
|---|---|
| Naproxen Sodium | 25.50 |
| Citric Acid | 4075 |
| PVP | 1.85 |
| PEG 400 | 30.25 |
| Water | 7.40 |
| PEG 600 | 30.25 |

Example 6. Naproxen Sodium with Hydrochloric Acid as the Deionizing Agent

Fill Material:

| Ingredients | % (by weight) |
|---|---|
| Naproxen Sodium | 25.50 |
| Hydrochloric Acid | 4072 |
| PVP | 1.85 |
| PEG 400 | 30.25 |
| Water | 7.40 |
| PEG 600 | 30.25 |

Example 7. Naproxen Sodium with Lactic Acid as the Deionizing Agent

Fill Material:

| Ingredients | % (by weight) |
|---|---|
| Naproxen Sodium | 27.50 |
| Lactic Acid | 5.27 |
| Propylene Glycol | 2.00 |
| PEG 400 | 64.64 |
| Water | 0.60 |

Example 8. Naproxen Sodium with Lactic Acid as the Deionizing Agent

Fill Material:

| Ingredients | % (by weight) |
|---|---|
| Naproxen Sodium | 25.00 |
| Lactic Acid | 0.24-0.35M |
| Propylene glycol | 2.00 |
| PEG 600. | q.s. |

Example 9. Naproxen Sodium with Lactic Acid as the Deionizing Agent

Fill Material:

| Ingredients | % (by weight) |
|---|---|
| Naproxen Sodium | 25.00 |
| Lactic Acid | 5.00 |
| Propylene glycol | 2.00 |
| PEG 600 | 61.2 |
| PEG 1000 | 6.80 |

Example 10. Naproxen Sodium with Lactic Acid as the Deionizing Agent

Fill Material:

| Ingredients | % (by weight) |
|---|---|
| Naproxen Sodium | 25.00 |
| Lactic acid | 5.00 |
| Propylene glycol | 2.00 |

-continued

| Ingredients | % (by weight) |
|---|---|
| PEG 600 | 51.00 |
| PEG 1000 | 17.00 |

Example 11. Naproxen Sodium with Lactic Acid as the Deionizing Agent

Fill Material:

| Ingredients | % (by weight) |
|---|---|
| Naproxen Sodium | 25.00 |
| Lactic Acid | 5.00 |
| Propylene glycol | 2.00 |
| PEG 600 | 34.00 |
| PEG 1000 | 34.00 |

Example 12. Naproxen Sodium with Lactic Acid as the Deionizing Agent

Fill Material:

| Ingredients | % (by weight) |
|---|---|
| Naproxen Sodium | 25.00 |
| Lactic acid | 5.00 |
| Propylene glycol | 2.00 |
| PEG 600 | 17.00 |
| PEG 1000 | 51.00 |

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the materials for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition comprising soft gelatin capsule comprising a fill material comprising:
   (a) a naproxen salt;
   (b) about 5% lactic acid by weight of the fill material; and
   (c) polyethylene glycol.

2. The composition of claim 1, wherein polyethylene glycol comprises about 10% to about 80% by weight of the fill material.

3. The composition of claim 1, wherein the polyethylene glycol comprises one or more polyethylene glycols comprising molecular weights between 300 and 1500.

4. The composition of claim 1, further comprising one or more excipients.

5. The composition of claim 4, wherein the excipients comprise plasticizers, crystallization inhibitors, wetting agents, bulk filling agents, bioavailability enhancers, solvents, pH-adjusting agents, dyes, preservatives, solvents, surfactants, or combinations thereof.

6. The composition of claim 1, further comprising a solubilizer selected from glycerin, polyvinylpyrrolidone, propylene glycol, or a combination thereof.

7. The composition of claim 6, wherein the solubilizer is present in amount from about 1% to about 10% by weight of the fill material.

8. A method of making the composition of claim 1, the method comprising the steps of:
   (i) mixing the naproxen salt, lactic acid, and polyethylene glycol at an appropriate temperature to form a fill material; and
   (ii) encapsulating the fill material in a soft gelatin capsule.

9. The method of claim 8, wherein the appropriate temperature is from about 50° C. to about 70° C.

10. A soft gelatin capsule comprising a fill material, the fill material comprising:
    (a) a naproxen salt;
    (b) about 5% lactic acid by weight of the fill material; and
    (c) polyethylene glycol.

11. The capsule of claim 10, wherein polyethylene glycol comprises about 10% to about 80% by weight of the fill material.

12. The capsule of claim 10, wherein the polyethylene glycol comprises one or more polyethylene glycols comprising molecular weights between 300 and 1500.

13. The capsule of claim 10, further comprising one or more excipients.

14. The capsule of claim 13, wherein the excipients comprise plasticizers, crystallization inhibitors, wetting agents, bulk filling agents, bioavailability enhancers, solvents, pH-adjusting agents, dyes, preservatives, solvents, surfactants, or combinations thereof.

15. The capsule of claim 10, further comprising a solubilizer selected from glycerin, polyvinylpyrrolidone, propylene glycol or a combination thereof.

16. The capsule of claim 15, wherein the solubilizer comprises about 1% to about 10% by weight of the fill material.

17. A method of using the capsule of claim 10 comprising administering to a patient in need thereof an effective amount of the capsule.

18. A soft gelatin capsule comprising a fill material comprising:
    (a) about 10% to about 80% by weight of the fill material polyethylene glycol having a molecular weight between 300 and 1500;
    (b) about 10% to about 50% by weight of the fill material naproxen sodium; and
    (c) about 5% of the fill material lactic acid.

19. A method of using the capsule of claim 18 comprising administering to a patient in need thereof an effective amount of the capsule.

20. A pharmaceutical composition prepared by a method comprising preparing a fill material comprising:
   mixing together
   (a) a naproxen salt;
   (b) about 5% by weight of the fill material lactic acid; and
   (c) polyethylene glycol having a molecular weight between 300 and 1500.

21. A soft gelatin capsule prepared by a method comprising:
   (a) producing a fill material by mixing:
      (i) a naproxen salt;
      (ii) about 5% by weight of the fill material lactic acid;
      (iii) polyethylene glycol having a molecular weight between 300 and 1500; and
   (b) encapsulating the mixture in a soft gelatin capsule.

22. The composition of claim 1, wherein the naproxen salt comprises sodium naproxen.

23. The composition of claim 6, wherein the solubilizer comprises polyvinylpyrrolidone.

24. The method of claim 8, wherein the naproxen salt comprises sodium naproxen.

25. A capsule produced by the method of claim 8.

26. The capsule of claim 10, wherein the naproxen salt comprises sodium naproxen.

27. The capsule of claim 15, wherein the solubilizer comprises polyvinylpyrrolidone.

28. The capsule of claim 18, wherein the fill further comprises a solubilizer.

29. The capsule of claim 28, wherein the solubilizer comprises about 1% to about 10% by weight of the fill material.

30. The capsule of claim 28, wherein the solubilizer comprises polyvinylpyrrolidone.

31. The method of claim 20, wherein the naproxen salt comprises sodium naproxen.

32. The method of claim 20, wherein the fill material further comprises a solubilizer.

33. The method of claim 32, wherein the solubilizer comprises about 1% to about 10% by weight of the fill material.

34. The method of claim 32, wherein the solubilizer comprises polyvinylpyrrolidone.

35. The capsule of claim 21, wherein the naproxen salt comprises sodium naproxen.

36. The capsule of claim 21, wherein the fill material further comprises a solubilizer.

37. The capsule of claim 36, wherein the solubilizer comprises about 1% to about 10% by weight of the fill material.

38. The capsule of claim 36, wherein the solubilizer comprises polyvinylpyrrolidone.

* * * * *